US009861645B2

(12) United States Patent
Kazin et al.

(10) Patent No.: US 9,861,645 B2
(45) Date of Patent: Jan. 9, 2018

(54) ANTI-ITCH SCALP TREATMENT COMPOSITIONS AND COMBINATIONS

(71) Applicant: RAK Holdings LLC, Baltimore, MD (US)

(72) Inventors: Rebecca Kazin, Baltimore, MD (US); Irwin A Palefsky, West Orange, NJ (US); Wanda Fontaine, Plainfield, NJ (US); Yamaris Melendez, Clifton, NJ (US)

(73) Assignee: RAK Holdings LLC, Baltimore, MD (US)

( * ) Notice: Subject to any disclaimer, the term of this patent is extended or adjusted under 35 U.S.C. 154(b) by 166 days.

(21) Appl. No.: 13/834,779

(22) Filed: Mar. 15, 2013

(65) Prior Publication Data

US 2014/0187518 A1    Jul. 3, 2014

Related U.S. Application Data

(60) Provisional application No. 61/747,163, filed on Dec. 28, 2012.

(51) Int. Cl.
```
A61K 31/60     (2006.01)
A61K 31/573    (2006.01)
A61K 45/06     (2006.01)
A61K 31/704    (2006.01)
A61K 36/76     (2006.01)
A61K 9/00      (2006.01)
A61K 8/368     (2006.01)
A61Q 5/00      (2006.01)
A61Q 5/02      (2006.01)
A61K 8/60      (2006.01)
A61K 8/63      (2006.01)
A61K 8/97      (2017.01)
```
(52) U.S. Cl.
CPC .............. *A61K 31/60* (2013.01); *A61K 8/368* (2013.01); *A61K 8/602* (2013.01); *A61K 8/63* (2013.01); *A61K 8/97* (2013.01); *A61K 9/0014* (2013.01); *A61K 31/573* (2013.01); *A61K 31/704* (2013.01); *A61K 36/76* (2013.01); *A61K 45/06* (2013.01); *A61Q 5/00* (2013.01); *A61Q 5/02* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 4,722,837 A * | 2/1988 | Cameron | 424/705 |
| 4,835,148 A * | 5/1989 | Barford et al. | 514/179 |
| 5,002,938 A * | 3/1991 | Wang | A61K 9/0014 514/171 |
| 5,635,469 A * | 6/1997 | Fowler | A61K 8/046 239/329 |
| 5,661,170 A | 8/1997 | Chodosh | |
| 5,667,800 A | 9/1997 | De Vringer | |
| 5,730,965 A * | 3/1998 | Rapaport | A61K 8/347 424/60 |
| 5,834,513 A | 11/1998 | Ptchelintsev et al. | |
| 6,071,541 A | 6/2000 | Murad | |
| 6,075,056 A * | 6/2000 | Quigley, Jr. | A61K 31/57 514/649 |
| 6,190,678 B1 | 2/2001 | Hasenoehrl et al. | |
| 6,207,694 B1 * | 3/2001 | Murad | A61K 8/345 514/396 |
| 6,217,913 B1 | 4/2001 | Mohammadi | |
| 6,271,246 B1 | 8/2001 | Murad | |
| 6,316,428 B1 | 11/2001 | Crandall | |
| 6,455,076 B1 | 9/2002 | Hahn et al. | |
| 6,573,301 B1 | 6/2003 | Glassman et al. | |
| 6,630,163 B1 | 10/2003 | Murad | |
| 6,649,155 B1 | 11/2003 | Dunlop | |
| 6,649,178 B2 | 11/2003 | Mohammadi et al. | |
| 6,680,062 B2 | 1/2004 | Muizzuddin et al. | |
| 6,974,569 B2 | 12/2005 | Dunlop | |
| 7,001,594 B1 | 2/2006 | Peffly | |
| 7,316,810 B1 | 1/2008 | Preuilh | |
| 7,407,666 B2 | 8/2008 | Tarletsky et al. | |
| 7,700,081 B2 | 4/2010 | Preuilh | |
| 8,178,106 B2 | 5/2012 | Hines et al. | |
| 8,377,663 B2 | 2/2013 | Lintner et al. | |
| 8,551,462 B2 | 10/2013 | Goldstein et al. | |
| 8,685,381 B2 | 4/2014 | Schlessinger et al. | |
| 8,815,308 B2 | 8/2014 | Florence et al. | |
| 9,072,739 B2 | 7/2015 | DeJovin | |
| 9,126,061 B2 | 9/2015 | Jacobs | |

(Continued)

FOREIGN PATENT DOCUMENTS

| EP | 0325949 A | 8/1989 |
|---|---|---|
| JP | 61183209 A | 8/1986 |

(Continued)

OTHER PUBLICATIONS

Scalpicin document (combe document, 2007, OTC labels 2011, 2012—all combined as one document).*
Siegenthaler (Importance of Skin's pH, 2004).*
JP-2003-321347—Document with English translation and Japanese document attached, 2003.*
Remington's: the Science and Practice of Pharmacy, Nineteenth edition, vol. 1, p. 806.*
Counterpart PCT Appln. No. PCT/US2013/078128 International Search Report, dated Mar. 31, 2014.

(Continued)

*Primary Examiner* — Umamaheswari Ramachandran
(74) *Attorney, Agent, or Firm* — Frost Brown Todd LLC

(57) ABSTRACT

Provided herein are sulfate free and/or sodium chloride free scalp treatment compositions comprising corticosteroid, combinations containing these compositions, kits and methods, particularly for treating and/or preventing itchy scalp.

6 Claims, No Drawings

(56) References Cited

U.S. PATENT DOCUMENTS

| | | | |
|---|---|---|---|
| 9,138,446 B2 | 9/2015 | Weisenfluh et al. | |
| 9,149,490 B2 | 10/2015 | Roszell | |
| 9,180,112 B2 | 11/2015 | Billis | |
| 2003/0007939 A1* | 1/2003 | Murad | A61K 8/22 424/61 |
| 2003/0232091 A1 | 12/2003 | Shefer et al. | |
| 2004/0156873 A1 | 8/2004 | Gupta | |
| 2005/0043283 A1 | 2/2005 | Fares | |
| 2005/0143324 A1* | 6/2005 | Mastrodonato | A61K 31/045 514/27 |
| 2005/0276830 A1 | 12/2005 | DeJovin et al. | |
| 2006/0165636 A1 | 7/2006 | Hasebe et al. | |
| 2008/0124409 A1 | 5/2008 | Zimmerman et al. | |
| 2009/0071493 A1* | 3/2009 | Nguyen | A61K 8/361 132/202 |
| 2009/0317502 A1* | 12/2009 | Crutchfield, III | 424/776 |
| 2011/0060195 A1 | 10/2011 | DeNoray | |
| 2011/0256249 A1* | 10/2011 | Campbell et al. | 424/735 |
| 2011/0139170 A1 | 11/2011 | Hippe | |
| 2012/0214776 A1* | 8/2012 | Ubaidulla | A61K 9/0014 514/174 |
| 2014/0073616 A1 | 3/2014 | Marder | |

FOREIGN PATENT DOCUMENTS

| | | |
|---|---|---|
| JP | 62205010 A | 9/1987 |
| JP | 2002-138045 A | 5/2002 |
| JP | 2005-239645 A | 9/2005 |
| WO | WO199406434 A1 | 3/1994 |
| WO | WO2005018587 A1 | 3/2005 |
| WO | WO 2005/030152 | 4/2005 |
| WO | WO2006092151 A1 | 9/2006 |

OTHER PUBLICATIONS

Counterpart PCT Appln. No. PCT/US2013/078128 Written Opinon, dated Mar. 31, 2014.

Grimalt, R. (2007). A Practical Guide to Scalp Disorders. Journal of Investigative Dermatology Symposium Proceedings 12: 10-14.

Schneeberg, M.D., N.G., et al., "Congenital Virilizing Adrenal Hyperplasia in Identical Twins", The Journal of Clinical Endocrinology & Metabolism, 1957. Abstract only.

Segaloff, M.D., A. "Hydrocortisone Acetate, A Long-Acting Corticoid vs. Hydrocortisone, A Short-Acting Corticoid", Letter to the Editor, The Journal of Clinical Endocrinology & Metabolism, 1959, 19(12), pp. 1682-1683.

Clobex Lotion, patient information, Manufactured by: DPT Laboratories, Ltd., Oct. 2005.

Clobex Shampoo, patient information, Manufactured by: G Production Inc., Nov. 2011.

Hagen, T.A., et al., "Permeation of Hydrocortisone and Hydrocortisone 21-Alkyl Esters Through Silicone Rubber Membranes—Relationship to Regular Solution Solubility Behavior," Journal of Membrane Science, 1987, vol. 30, pp. 47-65.

Housman, MD, T.S., et al., "The use of 0.25% zinc pyrithione spray does not enhance the efficacy of clobetasol propionate 0.05% foam in the treatment of psoriasis," J. Am Acad Dermatol, Jul. 2003, pp. 79-82.

Novack, K.M. ed., "Salicylic acid," Drug Facts and Comparisons, 59$^{th}$ Edition, 2005, Wolters Kluwer Health, St. Louis, Missouri, p. 2579.

Pires-Oliveira, R., et al., "UV-vis spectra as an alternative to the Lowry method for quantify hair damage induced by surfactants," Colloids and Surfaces B: Biointerfaces, 2014, vol. 123, pp. 326-330.

Polano, MD, M.K. et al., "Dependence of Corticosteroid Penetration in the Vehicle," Arch Dermatol—vol. 112, May 1976, pp. 675-680.

Provital Group, trikenol: Natural synergic complex for the treatment of dandruff, product information, Jan. 2013.

Trüeb, R., "Shampoos: Ingredients, efficacy and adverse effects," JDDG, May 2007, Band 5, pp. 356-365.

"10 Shampoos That Contain Salicylic Acid," Scalp Health, 2016, 7 pgs., accessed from http://www.nicehair.org/10-shampoos-contain-salicylic-acid/.

Hoyle, M.G., "Salicylic Acid for Dandruff," Livestrong.com, Oct. 29, 2015, 3 pgs., accessed from http://www.livestrong.com/article/186959-salicylic-acid-for-dandruff.

"What is Hydrocortisone/salicylic acid/sulfur topical?" everyday Health, Nov. 5, 2014, 5pgs., accessed from http://www.everydayhealth.com/drugs/hydrocortisone-salicylic-acid-sulfur-topical.

\* cited by examiner

ANTI-ITCH SCALP TREATMENT COMPOSITIONS AND COMBINATIONS

TECHNICAL FIELD

Provided herein are scalp treatment compositions, combinations, kits and methods, particularly for treating and/or preventing itchy scalp.

BACKGROUND

The role of the human scalp is to protect the head. As a result, it is the first point of contact with various agents that might cause scalp discomfort, particularly itching. Scalp itch and dryness are exceedingly common scalp conditions affecting almost half of the population at the post-pubertal age and of any sex and ethnicity. Causes of this common condition are multi-factorial. Dry skin of the scalp is the most common cause of itchy, flaking scalp. Irritated, oily scalp (ie seborrheic dermatitis) is another frequent cause of this common symptom triad. In addition, not shampooing often enough (common in patients with chemically treated hair) often causes these symptoms because oil and skin cells from your scalp build up, causing itching and flaking. Psoriasis and eczema patients often note these common scalp symptoms. Moreover, sensitivity to hair care products including hair straighteners and dye can cause a red, itchy, scaling scalp. In this case, shampooing too often with products not designed for color treated or straightened hair, may irritate the scalp, causing the above symptoms (reviewed in mayoclinic.com). Examples of treatment methods are disclosed in U.S. Pat. Nos. 7,316,810, 7,700,081, JP62205010, JP61183209, WO2005030152.

Concurrently and notably, the global market (professional and at home) for hair color is about $12B (Euromonitor) and growing. P&G claims that 92% of women in developed markets have colored their hair at some point. The beauty industry claims that number is about 80%. In addition, the hair straightening market is growing exponentially with the advent of milder no-lye straighteners safe for all hair types.

Paradoxically, shampoos and conditioners are historically formulated with the sulfate surfactant sodium lauryl sulfate and/or sodium laureth sulfate as well as sodium chloride, which is used to adjust the product's viscosity. However, as the prevalence of consumers with 'treated hair' (ie. colored and/or chemically straightened) has grown, consumers, stylists, and physicians have noted that this subset cannot use the available hair products (shampoos, conditioners, etc) on the global market because the sulfates and sodium chloride used to clean the hair, have been shown to produce dry, brittle, frizzy hair and prematurely strip hair color and chemical straighteners.

OBJECTS

It is evident that consumers are now investing increasing amounts of time and money in hair color and/or straightening treatments. Consumers who have 'treated' hair have an increased risk of developing scalp dryness, itching and flaking. Such consumers who seek medical attention commonly complain of the triad of scalp symptoms and seek treatment that treats the scalp without weakening the hair. Ironically, the only products on the market that can address their distressing and embarrassing scalp symptoms will worsen the appearance and strength of their hair. Clearly, there is a need for a hair care line designed to effectively treat the common scalp symptom triad without compromising the integrity of the hair color, texture, and shine. It is thus an object to provide such a hair treatment regimen.

SUMMARY OF DISCLOSURE

To address this large and continually expanding subset of consumers, provided is a unique hair care line designed to effectively treat the common scalp symptom triad without compromising the integrity of the hair color, texture, and shine. As will be set forth below, the formula comprises topical anti-inflammatory agents (corticosteroids) and replaces for the most part harsh sulfates and/or sodium chloride with safe, gentle, and effective agents that all consumers including those with 'treated hair' can safely use to treat their scalp AND their hair.

In particular, provided is a scalp treatment which is a substantially free of sodium chloride and/or sulfate composition having a pH between about 4.5 to about 7.5, particularly between about 5.0 to about 7.0 and more particularly between about 6.0 to about 7.0 comprising a corticosteroid between about 0.2% and about 20% by weight of a corticosteroid and at least one noncorticosteroid anti-itch and/or anti-inflammatory agent. It may be in the form of a shampoo, conditioner or scalp spot treatment. Further provided is a combination comprising (a) a shampoo; (b) conditioner and (c) scalp spot treatment composition, each of which comprises the scalp treatment set forth above. A kit comprising this combination and a set of instructions is additionally provided.

Furthermore, a method for modulating itching in a scalp in a human subject comprising applying to the scalp an amount of the composition or combination set forth above effective to modulate said itching.

DETAILED DESCRIPTION OF EMBODIMENTS

While the formulations, methods and systems heretofore are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

In the present specification, the terms "solution", "preparation", "composition" and "formulation" can be used interchangeably.

Where a range of values is provided, it is understood that each intervening value, to the tenth of the unit of the lower limit unless the context clearly dictates otherwise, between the upper and lower limit of that range and any other stated or intervening value in that stated range, is included therein. Smaller ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the preferred methods and materials are now described.

As used herein, "modulates" means to alter the degree and/or intensity of itching of the scalp.

As defined herein "substantially free" of sodium chloride and/or sulfate means that the composition contains no more than about 3% sodium chloride and/or sulfate, more particularly, no more than about 2.5% sodium chloride and/or sulfate, yet even more particular no more than about 2.0% sodium chloride and/or sulfate, yet even more particular no more than about 1.5% sodium chloride and/or sulfate, yet even more particular no more than about 1.0% sodium chloride and/or sulfate, yet even more particular no more than about 0.5% sodium chloride and/or sulfate, Compositions The compositions set forth herein as noted above comprise at least one corticosteroid and at least one non-corticosteroid anti-itch and/or anti-inflammatory agent. Furthermore the compositions may further comprise one or more: moisturizers, pH neutralizing agents, preservatives, anti-oxidants and fragrance. Further details regarding each these components are set forth below. In a more particular embodiment, the composition

TABLE I

| Substance | % By Weight |
| --- | --- |
| Corticosteroid | 0.5-2.0% |
| Non-corticosteroid anti-itch/anti-inflammatory | 0.10-0.50% |
| Humectant | 0.5-3.0% |
| Emollient | 0.25-2.0% |
| pH neutralizing agent | 0.0-1.0% |
| Preservative | 0.30-1.0% |
| Anti-oxidant | 0.05-0.2% |
| Fragrance | 0.1-1.0% |
| Thickener | 0.1-1.0% |
| Diluent | 60-85% |

The compositions are substantially sodium chloride free and sulfate free as set forth above. They may also be free of thiadiazolidines and/or aromatic fatty acids as active ingredients.

Corticosteroids

In a particular embodiment, the corticosteroid is a non-ester hydrocortisone type corticosteroid and may include but is not limited to hydrocortisone, hydrocortisone acetate, cortisone acetate, tixocortol pivalate, prednisolone, methylprednisolone, and prednisone, clobetasol propionate, fluocinolone acetonide, fluocinonide, betamethasone valerate, betamethasone dipropionate and flurandrenolide and hydrocortisone 17-butyrate. In a more particular embodiment, the corticosteroid is hydrocortisone or hydrocortisone acetate is present in the amount of between about 0.2 to about 2.0% by weight and in particular, between about 0.5 to about 1.5% by weight. In an even more particular embodiment, hydrocortisone or hydrocortisone acetate is present in the amount of about 0.5 to about 1.0% by weight.

Anti-Inflammatory Agents

The non-corticosteroid anti-inflammatory agents used in the may include but is not limited to pseudopterosins. In a particular embodiment, the pseudopterosins may be extracted from Caribbean Sea Whip and marketed as Gorgonian Extract by Lip Chemical CO. Other anti-inflammatory agents may include but are not limited to allantoin beta glucan, chamomile extract, Green tea, ECGC (active ingredient in Green Tea). The anti-inflammatory agent may be present in the amount of about 0.05-1.0% by weight. The anti-inflammatory agent will modulate inflammation in the scalp.

Anti-Itch Agent

Further provided is one or more agents that modulate itching of the scalp. Examples of anti-itch agents include, but are not limited to, willow bark extract or salicylic acid in the amount of about 0.01-2.0% by weight.

Moisturizers

A further ingredient of the compositions are one or more moisturizers. The moisturizers may act as emollients (has softening/soothing action) and/or humectants (absorbs water and holds in moisture). Examples of such moisturizers include, but are not limited to, polyols such as sorbitol, glycerin, propylene glycol, ethylene glycol, polyethylene glycol, caprylyl glycol, polypropylene glycol, 1,3-butane diol, hexylene glycol, butylene glycol, isoprene glycol, propane diol, xylitol; ethylhexyl palmitate; a triglyceride such as caprylic/capric triglyceride and fatty acid ester such as cetearyl isononanoate or cetyl palmitate. The moisturizers, in a particular embodiment may be present in the amount of about 0.25%-5.0% by weight.

pH Stabilizing Agent

The composition is effective at pH values between about 4.5 to about 7.5, particularly between about 5.0 to about 7.5 and more particularly between about pH 6 and pH 7. One of ordinary skill in the art may add appropriate pH adjusting ingredients to the compositions of the present invention to adjust the pH to an acceptable range. One example of such a pH stabilizing agent is an amino, such as triethanolamine NaOH, KOH.

Preservatives

One or more preservatives may be included in the compositions set forth herein. Examples of such preservatives comprise one or more glycerin containing compound (e.g., or ethylhexylglycerin or phenoxyethanol), benzyl alcohol, potassium sorbate, phenoxyethanol methylisothiazolinone, DMDM Hydantoin, sodium benzoate and/or grapefruit seed extract. The preservatives may be present in the amount of about 20 ppm (0.0020%)-1.0%.

Anti-Oxidants

The anti-oxidant may include, but is not limited to, a Vitamin E compound which, for example, may be tocopherol, a tocopherol ester such as tocopheryl acetate, tocopheryl succinate, tocopheryl nicotinate, tocopheryl linoleate or a mixture thereof. The anti-oxidant may also be butylated hydroxytoluene (BHT) or butylated hydroxyanisole. These anti-oxidants may be present in the amount of about 0.01 to about 0.10% by weight.

Chelator

The composition may further comprise a chelating agent, such as EDTA, NaEDTA or HEDTA. The chelating agent may be present in the amount of about 0.02 to about 0.2% by weight.

Fragrance

The fragrance used may be those fragrances known in the art that are commonly added to shampoos, conditioners or scalp treatment compositions and are commercially available. These include, but are not limited to, fragrances derived from, Softto, Citrus, Lemon, Jasmine, Rose, Santal, Musk, Osmanthus, Amber, Orchid, Cucumber, Green Tea, Green Apple, Grapefruit, Vanilla, Melon, Lavender, Violet, Lily, Peppermint, Almond, Aloe, Honey, Strawberry, Passion Fruit, Topical Fruit, Gardenia.

Diluents

The term "diluent" as used herein refers to substances that may be used to dilute the active ingredients, the corticosteroid, anti-itch and/or anti-inflammatory agent. Water is the preferred diluent. The formulations require use of greater than 1% water to be effective. In a particular embodiment, greater than five percent water is used, and more particularly, greater than 50% water is used.

Thickeners

Such thickeners comprise polyethylene glycol and/or polyacrylates and/or alkyl acrylate crosspolymers, as well as cellulosic thickeners and xanthan gum. The thickener(s) may be present in an amount of about 0.1-5% by weight and more particularly in the amount of about 0.2-1% by weight.

Product Forms

Compositions set forth herein are typically for topical application to the hair and/or scalp and may be formulated as a transparent or opaque an oil-in-water emulsion, a water-in-oil emulsion, or multiple emulsions, a lotion, cream, gel, serum as well as in the form of an aqueous, water-and-alcohol, or oil solution. They may also be applied to the area requiring treatment in aerosol form.

Hair and/or scalp care compositions may be rinse off products or leave on products. Rinse off products are intended to be substantially rinsed off the hair and/or the scalp of the user with water after use. Leave on products are intended not to be rinsed off the hair and/or the scalp of the user immediately after use (i.e, within at least the first 2 hours, preferably at least four hours, after application of the composition). Leave on products include, for example, lotions, solution and serum that are intended for topical application to the hair and/or the scalp. Rinse off compositions include shampoos and hair conditioners, as well as hair and/or scalp treatment products which are intended to be left on the hair and/or scalp for up to 2 hours (eg, 5 minutes to 2 hours) before being rinsed off.

Preferred product forms are shampoos, conditioners, and scalp spot treatment formulations.

Shampoo/Cleanser Compositions

Shampoo compositions will comprise the ingredients set forth above. Furthermore, the shampoo will typically comprise one or more anionic, amphoteric or nonionic cleansing surfactants which are cosmetically acceptable and suitable for topical application to the hair.

Examples of anionic and amphoteric surfactants include but are not limited to a taurate such as sodium lauroyl taurate, sodium methyl cocoyl taurate, sodium methyl lauroyl taurate, sodium methyl myristoyl taurate, sodium methyl oleoyl taurate, sodium methyl palmitoyl taurate sodium lauriminodipropionate, sodium lauroamphoacetate, sodium lauramido diacetate, sodium cocyl isethionate Nonionic surfactants which can be included in shampoo compositions are the alkyl polyglycosides (APGs). Typically, the APG is one which comprises an alkyl group connected (optionally via a bridging group) to a block of one or more glycosyl groups. Preferred APGs are defined by the following formula:

$$RO\text{-}(G)n$$

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerization, n, may have a value of from about 1 to about 10 or more. Preferably, the value of n lies in the range of from about 1.1 to about 2. Most preferably the value of n lies in the range of from about 1.3 to about 1.5.

The total amount of surfactant in shampoo compositions of the invention is generally from about 5-20% and preferably from about 8-15% percent by weight of the composition.

A cationic polymer may be included in shampoo compositions for enhancing conditioning performance of the shampoo.

The cationic polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof. Cationic conditioning polymers that can be used include cationic polysaccharide polymers, such as cationic cellulose derivatives, cationic starch derivatives, and cationic guar gum derivatives, such as guar hydroxypropyltrimonium chloride (commercially available from Rhone-Poulenc in their JAGUAR trademark series). Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

The cationic conditioning polymer will generally be present in compositions of the invention at levels of from 0.01 to 5, particularly from 0.05 to 1, more particularly from 0.08 to 0.5 percent by weight of the composition.

In a particular embodiment, the pH of a shampoo composition is between about 5 to about 7 and preferably between about 6 to about 7.

In another particular embodiment, the shampoo is sulfate free but may contain between about 0.5 to about 3.0% sodium chloride.

Hair Conditioner Compositions

Compositions may also be formulated as conditioners for the treatment of hair (typically after shampooing) and subsequent rinsing.

Hair conditioner compositions according to the invention will suitably comprise a cationic conditioning surfactant that is cosmetically acceptable and suitable for topical application to the hair. Such surfactants may include but are not limited to cetrimonium chloride, stearalkonium chloride, behenetrimonium chloride, amodimethicone.

In a particular embodiment, the pH of the hair conditioner composition is between about 4.5 to about 6.5 and particularly between about 5.0 to about 6.5.

In another particular embodiment, the conditioner is sulfate free but may contain between about 0.1 to about 1.0% sodium chloride.

Scalp Spot Treatment Compositions

The scalp spot treatment composition may be in the form of a solution, an oil or serum that can be applied to specific afflicted portions of the scalp using a dropper. It may also be applied as an aerosol. Scalp treatment compositions may comprise silicone conditioning agents. Suitable silicone conditioning agents include but are not limited to, polydiorganosiloxanes, in particular polydimethylsiloxanes which have the CTFA designation dimethicone. It may also comprise a adjuvant which may include but is not limited to dimethyl isosorbide, ethanol, isopropanol, ethoxydiglycol, propylene glycol, 1,3 propanediol, butylene glycol.

In a particular embodiment, the pH of the scalp spot composition is between about 5.5 to about 7.5 and particularly between about 6 to about 7.

In another particular embodiment, the scalp spot treatment is sulfate free but may contain between about 0.1 to about 1.0% sodium chloride.

Scalp Treatment Combinations, Systems and Kits

The compositions set forth above may be applied singly. Alternatively they may applied as a combination. In a particular embodiment, the shampoo, conditioner and scalp treatment composition may be packaged along with instructions for use into a kit. In a particular embodiment, one may treat the scalp with the scalp treatment composition and then apply shampoo and optionally conditioner. Generally conditioner is applied simultaneously with shortly after, within about 5 to about 15 minutes of the shampoo application. The scalp treatment composition may be applied between shampoo applications

EXAMPLES

While not intended to limit in any way the scope of the present invention, the following examples demonstrate embodiments of the formulations and methods within the present invention. The use of the formulations hereinafter disclosed is not intended to be limited in any way by the characteristics of the hair tested in the following examples.

TABLE II

Scalp Treatment Cleanser (Shampoo)

| NO. | PHASE | FUNCTION | INCI DESIGNATION | % BY WEIGHT |
| --- | --- | --- | --- | --- |
| 1 | A | DILUENT | WATER (AQUA) | 30.35 |
| 2 | A | THICKENER | ACRYLATES/C10-30 ALKYL ACRYLATE CROSSPOLYMER | 0.80 |
| 3 | A | PH NEUTRALIZER | SODIUM HYDROXIDE WATER | 0.30 |
| 4 | A1 | DILUENT | WATER (AQUA) | 7.50 |
| 5 | A1 | CHELATING AGENT | DISODIUM EDTA | 0.10 |
| 6 | A1 | CONDITIONING AGENT | GUAR HYDROXYPROPYLTRIMONIUM CHLORIDE | 0.35 |
| 7 | A1 | ANTI-FLAMMATORY | ALLANTOIN | 0.10 |
| 8 | B | SURFACTANT | WATER SODIUM COCOYL ISETHIONATE SODIUM LAUROAMPHOACETATE SODIUM METHYL COCOYL TAURATE | 45.00 |
| 9 | B | SURFACTANT | DECYL GLUCOSIDE | 2.00 |
| 10 | B | FOAMING AGENT | COCAMIDOPROPYL BETAINE | 5.00 |
| 11 | B | OPACIFIER | GLYCOL STEARATE STEARAMIDE AMP | 1.50 |
| 12 | C | HUMECTANT | GLYCERIN | 1.00 |
| 13 | C | HUMECTANT | BUTYLENE GLYCOL | 2.00 |
| 14 | C | EMOLLIENT | GLYCERETH-26 | 2.00 |
| 15 | C | ANTI-FLAMMATORY | CAPRYLIC/CAPRIC TRIGLYCERIDE SEA WHIP EXTRACT | 0.10 |
| 16 | C | ANTI-FLAMMATORY | HYDROCORTISONE ACETATE | 1.00 |
| 17 | C | ANTI-OXIDANT | BHT | 0.10 |
| 18 | D | FRAGRANCE | FRAGRANCE | 0.25 |
| 19 | D | PRESERVATIVE | PHENOXYETHANOL METHYLISOTHIAZOLINONE | 0.25 | pH: 6.56

This formulation may be used as needed with warm water. A quarter sized amount of product and one lathering may be sufficient. If the scalp is extremely oily or hair has significant product buildup, a second washing may be used. Massage lather from the product gently into the scalp and rinse thoroughly.

Conditioning Treatment

The conditioner may have the following composition:

1% Hydrocortisone
Salicylic Acid
Sea Whip Extract
Allantoin
Vitamin E
Manuka Concentrate
Oat Kernel Extract
Ultraviolet Absorber In particular, the conditioner may have the following composition:

TABLE III

| | | | CONDITIONER | |
|---|---|---|---|---|
| NO. | PHASE | FUNCTION | INCI DESIGNATION | % BY WEIGHT |
| 1 | A | DILUENT | WATER (AQUA) | 68.60 |
| 2 | A | SLIP AGENT | | 0.50 |
| 3 | A | HUMECTANT | GLYCERIN | 0.75 |
| 4 | A | ANTI-FLAMMATORY | ALLANTOIN | 0.02 |
| 5 | B | CONDITIONING EMULSIFIER | BEHENTRIMONIUM CHLORIDE | 2.00 |
| 6 | B | STRUCTURING AGENT | CETEARYL ALCOHOL | 8.00 |
| 7 | B | CONDITIONING EMULSIFIER | DISTEARYLDIMONIUM CHLORIDE | 1.00 |
| 8 | B | CONDITIONER | DIMETHICONE | 1.00 |
| 9 | B | ANTIOXIDANT | TOCOPHERYL ACETATE | 0.10 |
| 10 | B | CONDITIONER | BIS-CETEARYL AMODIMETHICONE | 3.30 |
| 11 | B | CONDITIONER | DICETYLDIMONIUM CHLORIDE | 3.20 |
| 12 | B | CONDITIONER | CAPRYLIC/CAPRIC TRIGLYCERIDE | 0.20 |
| 13 | C | SCALP TREATMENT | SEA WHIP EXTRACT LEPTOSPERMONE ISOLEPTOSPERMONE FLAVESONE SALIX ALBA (WILLOW) | 0.50 |
| 14 | C | FRAGRANCE | FRAGRANCE | 1.0 |
| 15 | C | ANTI-FLAMMATORY | WATER GLYCERIN AVENA SATIVA (OAT) KERNEL EXTRACT WATER GLYCERIN ORYZA SATIVA (RICE) SEED PROTEIN PHYTIC ACID | 0.50 |
| 16 | C | UV PROTECTING | ORYZA SATIVA (RICE) EXTRACT | 0.50 |
| 17 | D | PRESERVATIVE | PHENOXYETHANOL METHYLISOTHIAZOLINONE | 0.55 |
| 18 | E | ANTI-ITCH | HYDROCORTISONE ACETATE | 1.00 |
| 19 | E | SOLVENT | SD-ALCOHOL 40-A | 5.00 |
| 20 | E | SOLVENT DELIVERY SYSTEM | DIMETHYL ISOSORBIDE | 2.00 |
| 21 | F | PH ADJUSTOR | SODIUM HYDROXIDE WATER | 0.15 |
| 22 | F | PH ADJUSTOR | CITRIC ACID | 0.15 | pH 5.84
PHASE A DISPERSE SLIP AGENT INTO WATER PHASE MIX UNTIL UNIFORM.
HEAT TO 80-85 C. AND ADD REMAINING PHASE A INGREDIENTS WITH MIXING
PHASE B COMBINE PHASE B INGREDIENTS AND HEAT WITH MIXING TO 80-85 C.
UNTIL WAXES MELT. AND ADD PHASE B TO PHASE A. MIX UNTIL UNIFORM.
COOL TO 60 C. WHILE STIRRING.
COOL TO 40 C.
PHASE C ADD PHASE C TO BATCH WITH MIXING. COOL TO RT
PHASE D ADD PHASE D TO BATCH WITH MIXING
PHASE E MIX PHASE E UNTIL THE HYDROCORTISONE DISSOLVES. ADD PHASE D TO BATCH WITH MIXING
PHASE F ADJUST PH TO 4.5-5.5 WITH PHASE F

This conditioner may be in the form of a luxurious, rich, nourishing cream. After towel drying hair, the product may be massaged into the scalp. The product is worked through the hair to the ends. For normal hair, leave on one minute and rinse with warm water. For damaged, processed, needy hair, leave on three to five minutes and rinse with warm water.

Scalp Spot Treatment

TABLE IV

| | | SCALP SPOT TREATMENT A | | |
|---|---|---|---|---|
| NO. | PHASE | FUNCTION | INCI DESIGNATION | % BY WEIGHT |
| 1 | A | | WATER (AQUA) | 50.25 |
| 2 | A | THICKENER | ACRYLATES/C10-30 ALKYL ACRYLATE CROSSPOLYMER | 0.40 |
| 3 | A | CHELATING AGENT | DISODIUM EDTA | 0.10 |
| 4 | A | HUMECTANT | GLYCERIN | 1.00 |
| 5 | A | HUMECTANT | PROPANEDIOL | 1.00 |

TABLE IV-continued

SCALP SPOT TREATMENT A

| NO. | PHASE | FUNCTION | INCI DESIGNATION | % BY WEIGHT |
|---|---|---|---|---|
| 6 | B | ADJUVANT | DIMETHYL ISOSORBIDE | 3.00 |
| 7 | B | ANTI-ITCH | HYDROCORTISONE | 1.00 |
| 8 | B | SOLVENT | SD ALCOHOL 40 | 40.00 |
| 9 | B | CONDITIONING | PEG-12 DIMETHICONE | 1.00 |
| 10 | B | ANTI-OXIDANT | TOCOPHERYL ACETATE | 0.10 |
| 11 | B | ANTI-INFLAMMATORY | BUTYLENE GLYCOL SEA WHIP EXTRACT | 0.20 |
| 12 | B | FRAGRANCE | FRAGRANCE METHYLPROPANEDIOL | 0.50 |
| 13 | C | ANTI-ITCH | POLYSORBATE 80 WATER SALICYLIC ACID LEPTOSPERMONE ISOLEPTOSPERMONE FLAVESONE *SALIX ALBA* (WILLOW) BARK EXTRACT | 0.50 |
| 14 | D | PH ADJUSTOR | TRIETHANOLAMINE | 0.40 |
| 15 | E | PRESERVATIVE | PHENOXYETHANOL METHYLISOTHIAZOLINONE | 0.55 |

Manufacturing Instructions:
PHASE A THOROUGHLY DISPERSE THE THICKENER IN WATER. HEAT TO 60-65 C. AND ADD REMAINDER OF PHASE A INGREDIENTS ONE AT A TIME. WHEN ALL DISSOLVED COOL WITH MIXING TO 35-40 C.
PHASE B COMBINE HYDROCORTISONE AND DIMETHYL ISOSORBIDE OF PHASE B AND DISSOLVE HYDROCORTISONE, THEN ADD TO ALCOHOL. ADD REMAINDER OF PHASE B ONE AT A TIME WHILE MIXING. MIX UNTIL ALL INGREDIENTS ARE DISSOLVED.
PHASE C ADD PHASE C TO BATCH
PHASE D ADD PHASE D TO BATCH WITH MIXING
PHASE E ADD PHASE E TO VESSEL WITH MIXING
ADJUST PH TO 5.5-7.0 WITH TEA IF NECESSARY; pH: 6.09

TABLE V

SCALP SPOT TREATMENT B

| NO. | PHASE | FUNCTION | INCI DESIGNATION | % BY WEIGHT |
|---|---|---|---|---|
| 1 | A |  | WATER (AQUA) | 49.40 |
| 2 | A | THICKENER | ACRYLATES/C10-30 ALKYL ACRYLATE CROSSPOLYMER | 0.60 |
| 3 | A | ANTI-INFLAMMATORY | ALLANTOIN | 0.02 |
| 4 | A | CHELATING AGENT | DISODIUM EDTA | 0.10 |
| 5 | A | HUMECTANT | GLYCERIN | 1.00 |
| 6 | A | HUMECTANT | PROPANEDIOL | 1.00 |
| 7 | B | ADJUVANT | DIMETHYL ISOSORBIDE | 3.00 |
| 8 | B | ANTI-ITCH | HYDROCORTISONE | 1.00 |
| 9 | B | SOLVENT | SD ALCOHOL 40 | 40.00 |
| 10 | B | CONDITIONING | PEG-12 DIMETHICONE | 1.00 |
| 11 | B | ANTI-OXIDANT | TOCOPHERYL ACETATE | 0.10 |
| 12 | B | ANTI-INFLAMMATORY | BUTYLENE GLYCOL SEA WHIP EXTRACT METHYLPROPANEDIOL | 0.20 |
| 13 | C | ANTI-ITCH | POLYSORBATE 80 WATER SALICYLIC ACID LEPTOSPERMONE ISOLEPTOSPERMONE FLAVESONE *SALIX ALBA* (WILLOW) BARK EXTRACT | 0.50 |
| 14 | C | ANTI-INFLAMMATORY | WATER GLCERIN *AVENA SATIVA* (OAT) KERNE EXTRACT | 1.00 |
| 15 | D | PH ADJUSTOR | TRIETHANOLAMINE | 0.53 |
| 16 | E | PRESERVATIVE | PHENOXYETHANOL METHYLISOTHIAZOLINONE | 0.55 |

Manufacturing Instructions:
PHASE A THOROUGHLY DISPERSE THE THICKENER IN WATER. HEAT TO 60-65 C. AND ADD REMAINDER OF PHASE A INGREDIENTS ONE AT A TIME. WHEN ALL DISSOLVED COOL WITH MIXING TO 35-40 C.
PHASE B COMBINE HYDROCORTISONE AND DIMETHYL ISOSORBIDE OF PHASE B AND DISSOLVE HYDROCORTISONE, THEN ADD TO ALCOHOL. ADD REMAINDER OF PHASE B ONE AT A TIME WHILE MIXING. MIX UNTIL ALL INGREDIENTS ARE DISSOLVED.
PHASE C ADD PHASE C TO BATCH
PHASE D ADD PHASE D TO BATCH WITH MIXING
PHASE E ADD PHASE E TO VESSEL WITH MIXING
ADJUST PH TO 6.0-7.0 WITH TEA IF NECESSARY; pH: 6.09

The formulation may be in the form of a gel and can be applied to specific spots on the scalp as needed. It can be dabbed on irritated areas without disturbing hair and will not run.

Although this invention has been described with reference to specific embodiments, the details thereof are not to be construed as limiting, as it is obvious that one can use various equivalents, changes and modifications and still be within the scope of the present invention.

Various references are cited throughout this specification, each of which is incorporated herein by reference in its entirety.

What is claimed is:

1. A scalp treatment composition consisting essentially of
    a) from about 0.2% to about 2.5% by weight hydrocortisone acetate;
    b) from about 0.01% to about 2.0% by weight salicylic acid;
    c) from about 0.05% to about 1.0% by weight allantoin;
    d) from about 0.05% to about 1.0% by weight gorgonian extract; and
    e) water in an amount of greater than about 50%;
    wherein said scalp treatment composition is substantially free of sodium chloride and sulfates;
    wherein said scalp treatment composition has a pH from about 4.5 to about 7.5; and
    wherein said scalp treatment composition is formulated for use as a rinse-off composition.

2. The composition according to claim 1, wherein said composition is a shampoo having a pH of from about 6 to about 7, or a hair conditioner having a pH of from about 5.0 to about 6.5.

3. The composition of claim 1, wherein the rinse-off scalp treatment composition is a shampoo and additionally comprises from about 5% to about 20% by weight of one or more anionic, amphoteric, or nonionic surfactants.

4. The composition of claim 1, wherein the rinse-off scalp treatment composition is a hair conditioner and comprises an effective amount of a cationic conditioning surfactant.

5. A method for modulating itching on the scalp of a human subject, comprising applying to the scalp an effective amount of the composition of claim 1, allowing the composition to remain on the scalp for up to two hours, and rinsing off substantially all of said composition from the scalp and hair.

6. A kit comprising the composition of claim 1 and instructions for use as a rinse-off product.

* * * * *